United States Patent

Yang et al.

[11] Patent Number: 6,071,913
[45] Date of Patent: Jun. 6, 2000

[54] ANGIOTENSIN II RECEPTOR ANTAGONISTIC 1,2,4-TRIAZIN-5-ONE DERIVATIVES

[75] Inventors: Paw-Hwa Yang, Taoyuan; Pei-Ling Lee, Taipei; Shan-Yen Chou, Taipei; Chia-Lin Wang, Taipei; Hsiao-Hwa Lu, Taipei, all of Taiwan

[73] Assignee: Development Center for Biotechnology, Taiwan

[21] Appl. No.: 08/987,039

[22] Filed: Dec. 9, 1997

[30] Foreign Application Priority Data

Mar. 28, 1997 [TW] Taiwan ................ 86103987

[51] Int. Cl.[7] .......... C07D 253/065; A61K 31/53
[52] U.S. Cl. .......... 514/242; 544/182; 544/319; 544/179; 514/269; 514/183
[58] Field of Search ............ 544/182, 328, 544/333; 514/242, 269, 256

[56] References Cited

U.S. PATENT DOCUMENTS

| | | | |
|---|---|---|---|
| 4,880,804 | 11/1989 | Carini et al. | 514/234.5 |
| 5,225,408 | 7/1993 | Weller, III | 514/229.2 |
| 5,534,534 | 7/1996 | Makino et al. | 514/388 |

FOREIGN PATENT DOCUMENTS

| | | |
|---|---|---|
| 253310A2 | 1/1988 | European Pat. Off. |
| 412848A2 | 2/1991 | European Pat. Off. |
| 446062A1 | 9/1991 | European Pat. Off. |
| 542059A1 | 5/1993 | European Pat. Off. |
| 547442A1 | 6/1993 | European Pat. Off. |
| 5155884 | 6/1993 | Japan. |

*Primary Examiner*—Mukund J. Shah
*Assistant Examiner*—Ann M. Kessinger
*Attorney, Agent, or Firm*—McDonnell Boehnen Hulbert & Berghoff

[57] ABSTRACT

Disclosed are novel 1,2,4-triazin-5-one biphenyl derivatives having structural formula (I) useful as non-peptide antagonists of angiotensin II receptor:

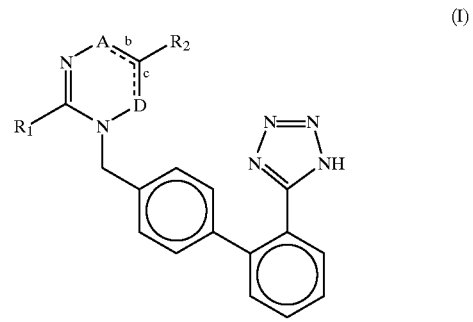

where $R_1$ represents alkyl, cycloalkyl, or substituted or unsubstituted aryl;

$R_2$ represents alkyl, substituted or unsubstituted aryl, or arylalkyl;

A and D independently represent $C-R_3$, N, NH or $C=O$, wherein when A and D independently denote $C-R_3$ or N, b and c are independently a double bond, and when A and D independently denote NH or $C=O$, b and c are independently a single bond; provided that b and c are not both double bonds; and $R_3$ is hydrogen, dialkylphosphonate or halogen;

and pharmaceutically acceptable salts thereof.

Also disclosed is the use of the compounds of formula (I) as non-peptide antagonists of angiotensin II receptor, in the treatment of cardiovascular diseases, in particular hypertension and congestive heart failure.

5 Claims, No Drawings

ANGIOTENSIN II RECEPTOR ANTAGONISTIC 1,2,4-TRIAZIN-5-ONE DERIVATIVES

FIELD OF THE INVENTION

The present invention relates to novel non-peptide antagonists of angiotensin II receptor, and to use of the antagonists in the treatment of cardiovascular diseases, especially hypertension and congestive heart failure.

BACKGROUND OF THE INVENTION

The morbidity of chronic cardiovascular diseases in senile population has increased in the recent years. The most common chronic disease in senile population is hypertension.

Most of the effective methods for treating hypertension which have been developed as far relate to the inhibition of renin-angiotensin system (RAS), because RAS plays a central role in the regulation of blood pressure. In mammals, the elevation of blood pressure results from the production of an octapeptide hormone called angiotensin II in RAS from the cleavage of a decapeptide called angiotensin I by angiotensin converting enzyme (ACE). Accordingly, the inhibition of ACE provides a way for treating hypertension.

In the past twenty years, the most effective pharmaceuticals for hypertension therapy are ACE inhibitors, e.g. CAPOTEN® marketed by Bristol-Myers Co. and RENITEC® by Merck Sharp & Dohme Co.

The structural formulae of the active ingredients in the above products are depicted below:

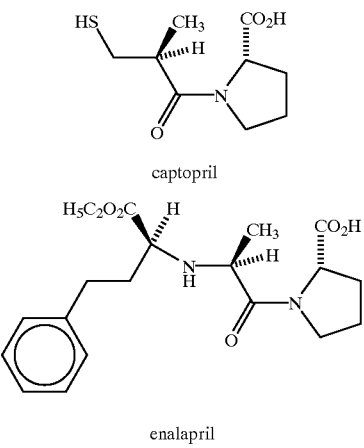

ACE inhibitors, however, disadvantageously lack selectivity, and normally cleave other physiologically important peptides, causing side effects such as dry cough and vascular edema.

Another way for treating hypertension is to directly block the receptor of angiotensin II. Many peptide derivatives which mimic the action of angiotensin II are proposed for the antagonists of angiotensin II receptor. However, these peptide derivatives lack oral, exhibit partial agonist and lack long period of efficacy.

Recently, a more effective way for treating hypertension has been developed in the art, i.e. non-peptide antagonists of angiotensin II receptor. For example, the benzimidazole derivatives disclosed in U.S. Pat. No. 4,880,804; the oxadiazinone derivatives disclosed in U.S. Pat. No. 5,225,408; the imidazole derivatives described in EP-A 253 310; the quinoline derivatives disclosed in EP-A 412 848; the carbon-linked pyrazole derivatives disclosed in EP-A 446 062; the dihydropyrimidine derivatives disclosed in EP-A 547 442; the diphenylpyridinone derivatives disclosed in EP-A 542 059; and the condensed pyrazine derivatives disclosed in Japan Laid-Open Patent 5-155884. The above patents in their entirety are incorporated herein as the references of the invention.

Because the high morbidity of chronic cardiovascular diseases such as hypertension and congestive heart failure has increased in the recent years, developments of other novel non-peptide antagonists of angiotensin II receptor are of necessity.

One object of the invention is to provide novel non-peptide antagonists of angiotensin II receptor.

Another object of the invention is to provide a method for treating cardiovascular diseases, in particular hypertension and congestive heart failure.

A further object of the invention is to provide a pharmaceutical composition useful in the treatment of cardiovascular diseases, in particular hypertension and congestive heart failure.

SUMMARY OF THE INVENTION

It has been surprisingly found that compounds of formula (I) and their pharmaceutically acceptable salts effectively bond to angiotensin II receptor, rendering them useful as potent antagonists of angiotensin II receptor:

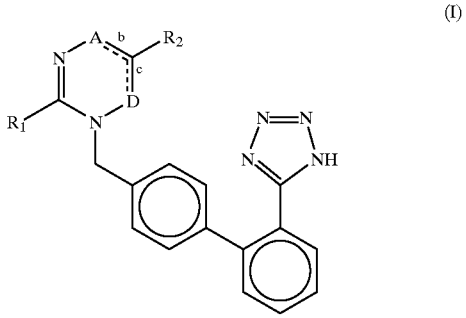

where
  $R_1$ represents alkyl, cycloalkyl, or substituted or unsubstituted aryl;
  $R_2$ represents alkyl, substituted or unsubstituted aryl, or arylalkyl;
  A and D independently represent C—$R_3$, N, NH or C=O, wherein when A and D independently denote C—$R_3$ or N, b and c are independently a double bond, and when A and D independently denote NH or C=O, b and c are independently a single bond; provided that b and c are not both double bonds; and
  $R_3$ is hydrogen, dialkylphosphonate or halogen;
and pharmaceutically acceptable salts thereof.

In one aspect of the invention there is provided the compounds of formula (I) and their pharmaceutically acceptable salts.

In another aspect of the invention there is provided the use of the compounds of formula (I) as antagonists of angiotensin II receptor.

In a further aspect of the invention there is provided a method for the treatment of cardiovascular diseases, which comprises administering an effective amount of the compounds of formula (I) to a subject in need of such treatment.

In a further aspect of the invention there is provided a pharmaceutical composition useful in the treatment of cardiovascular diseases, which comprises an effective amount of the compounds of formula (I) or their pharmaceutically acceptable salts as the active ingredient and a pharmaceutically acceptable carrier, excipient and diluent thereof.

DETAILED DESCRIPTION OF THE INVENTION

In the first aspect of the invention there is provided 1,2,4-triazin-5-one biphenyl derivatives having the structural formula (I):

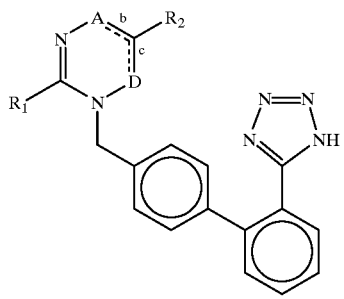

where
- R$_1$ represents alkyl, cycloalkyl, or substituted or unsubstituted aryl;
- R$_2$ represents alkyl, substituted or unsubstituted aryl, or arylalkyl;
- A and D independently represent C—R$_3$, N, NH or C=O, wherein when A and D independently denote C—R$_3$ or N, b and c are independently a double bond, and when A and D independently denote NH or C=O, b and c are independently a single bond; provided that b and c are not both double bonds; and
- R$_3$ is hydrogen, dialkylphosphonate or halogen;

and pharmaceutically acceptable salts thereof.

The term "alkyl" used herein as an independent word or as a part of a word refers to a branched or unbranched saturated acyclic aliphatic group. Preferably, the alkyl group in accordance with the invention has 1 to 8 carbon atoms. Examples of such group include, but not limited to, methyl, ethyl, n-propyl, i-propyl, n-butyl, i-butyl, 2-butyl, and t-butyl.

The term "cycloalkyl" as used herein refers to a saturated cyclic aliphatic group. Preferably, the cycloalkyl group in accordance with the invention has 3 to 8 carbon atoms. Examples of such group include, but not limited to, cyclopropyl, cyclobutyl, cyclopentyl, and cyclohexyl.

The term "aryl" used herein as an independent word or a part of a word refers to an aromatic group. Examples of such group includes, but not limited to, phenyl, and naphthyl.

Accordingly, examples of "arylalkyl" include, but not limited to, benzyl, and phenylethyl.

As used herein, the term "halogen" refers to a halo radical which includes, but not limited to, fluoro, chloro, and bromo.

For illustrative purpose, the compounds of formula (I) may be selected from the group consisting of, but not limited to:
- 6-methyl-3-phenyl-5-oxo-2-[[2'-(1H-tetrazol-5-yl)biphenyl-4-yl]methyl]-1,2,4-triazine;
- 6-methyl-3-phenyl-5-oxo-4-[[2'-(1H-tetrazol-5-yl)biphenyl-4-yl]methyl]-1,2,4-triazine;
- 3,6-diphenyl-5-oxo-2-[[2'-(1H-tetrazol-5-yl)biphenyl-4-yl]methyl]-1,2,4-triazine;
- 3,6-diphenyl-5-oxo-4-[[2'-(1H-tetrazol-5-yl)biphenyl-4-yl]methyl]-1,2,4-triazine;
- 6-(2'-phenylethyl)-3-phenyl-5-oxo-2-[[2'-(1H-tetrazol-5-yl)biphenyl-4-yl]methyl]-1,2,4-triazine;
- 6-methyl-3-butyl-5-oxo-2-[[2'-(1H-tetrazol-5-yl)biphenyl-4-yl]methyl]-1,2,4-triazine;
- 6-methyl-3-butyl-5-oxo-4-[[2'-(1H-tetrazol-5-yl)biphenyl-4-yl]methyl]-1,2,4-triazine;
- 6-phenyl-3-butyl-5-oxo-2-[[2'-(1H-tetrazol-5-yl)biphenyl-4-yl]methyl]-1,2,4-triazine;
- 6-phenyl-3-butyl-5-oxo-4-[[2'-(1H-tetrazol-5-yl)biphenyl-4-yl]methyl]-1,2,4-triazine;
- 6-benzyl-3-butyl-5-oxo-2-[[2'-(1H-tetrazol-5-yl)biphenyl-4-yl]methyl]-1,2,4-triazine;
- 6-(2'-phenylethyl)-3-butyl-5-oxo-2-[[2'-(1H-tetrazol-5-yl)biphenyl-4-yl]methyl]-1,2,4-triazine; and
- 6-(2'-phenylethyl)-3-butyl-5-oxo-4-[[2'-(1H-tetrazol-5-yl)biphenyl-4-yl]methyl]-1,2,4-triazine.

The compounds of formula (I) and their pharmaceutically acceptable salts may be produced in the following manner:

(1) reacting the following 1,2,4-triazin-5-one compounds

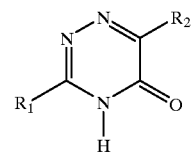

where R$_1$ and R$_2$ are as defined above, with 2-(triphenylmethyl)-5-[4'-(bromomethyl)biphenyl-2-yl]tetrazole under basic conditions to form the following compounds

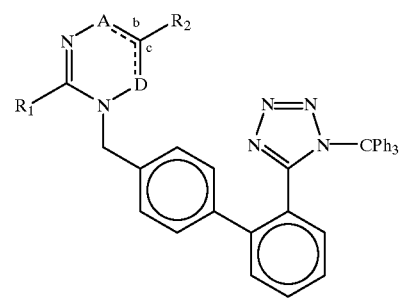

where R$_1$, R$_2$, A, b, c and D are as defined above;

(2) deprotecting the compounds obtained in step (1) under acidic conditions to form the compounds of formula (I);

(3) if desired, converting the compounds of formula (I) into corresponding pharmaceutically acceptable salts thereof.

For illustrative purpose, the compounds of formula (I) can be synthesized as depicted in Schemes 1 to 4 below.

Scheme 1

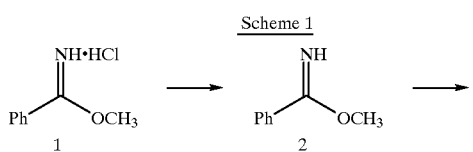

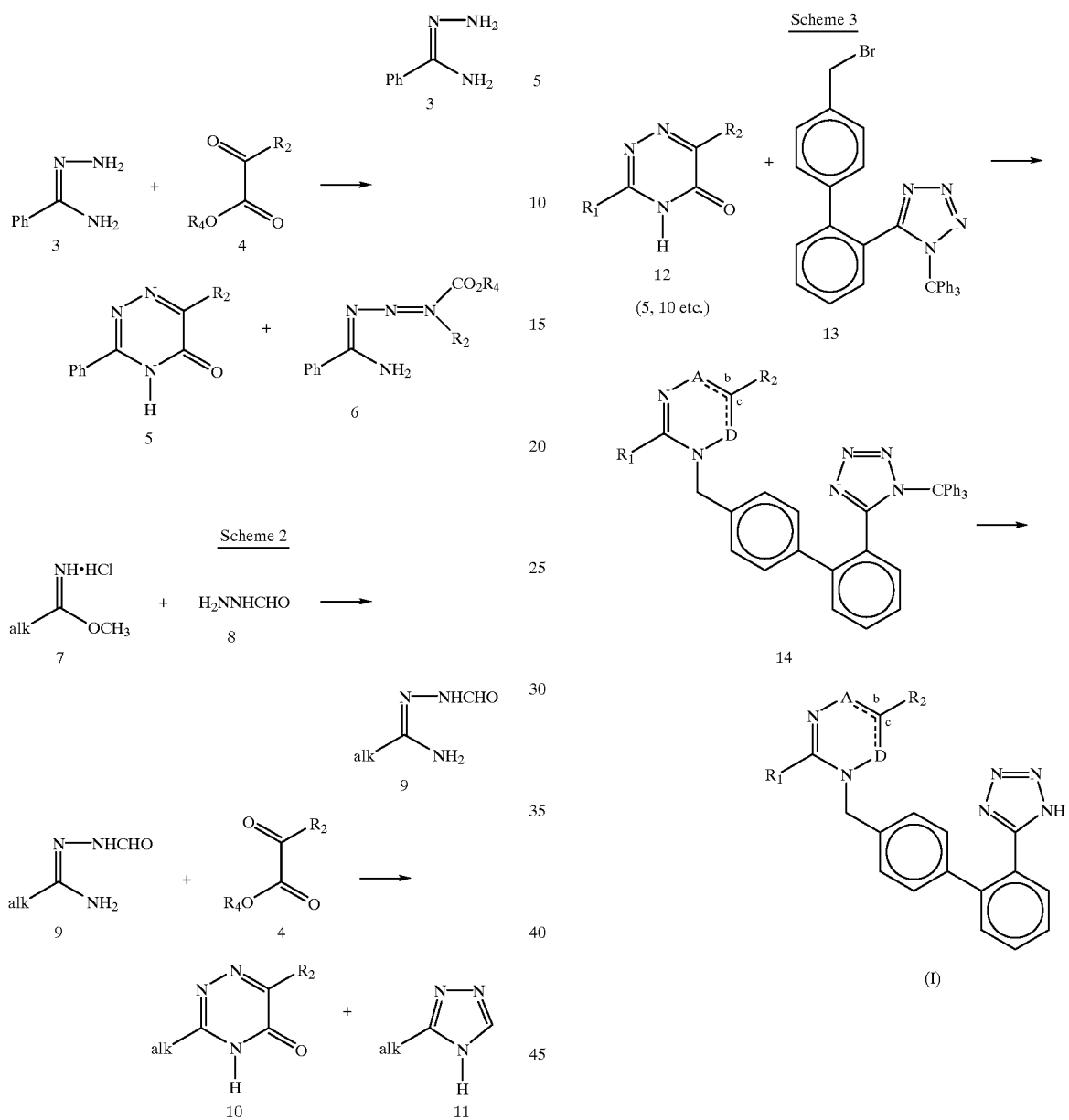
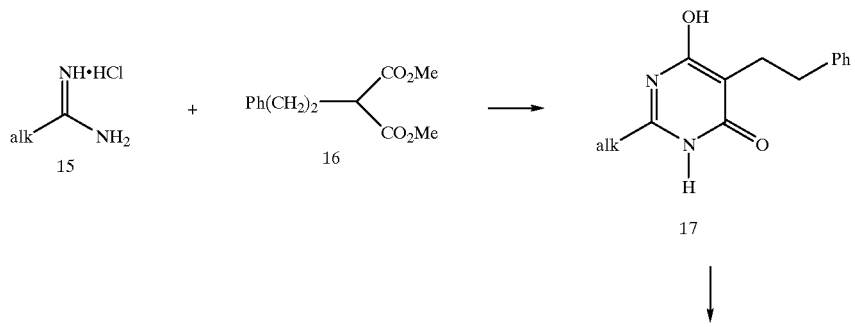

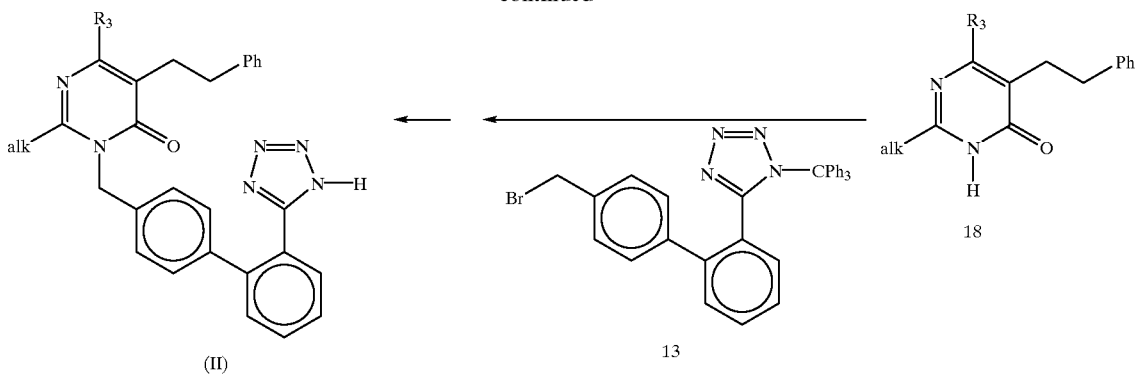

As shown in Scheme 1, benzimino ester hydrochloride 1 can be first neutralized with a base (e.g. 5% sodium hydroxide) to obtain the corresponding benzimino ester free base 2. Compound 2 can then react with anhydrous hydrazine to produce hydrazidine 3, and the latter can be cyclized with (α-keto compound 4 wherein $R_2$ has the meanings as defined for the compounds of formula (I) and $R_4$ is H or alkyl under reflux in isopropanol or dimethyl formamide (DMF) to produce the cyclic 1,2,4-triazin-5-one 5 (intermediate) and acyclic compound 6.

As shown in Scheme 2, the reaction of alkyl imino ester hydrochloride 7 and formyl hydrazide 8 in the presence of a base (such as triethylamine) results in alkyl formyl hydrazidine 9. Thereafter, compound 9 can be cyclized with compound 4 under reflux in isopropanol or DMF to produce another cyclic 1,2,4-triazin-5-one 10 (intermediate) and alkyl 1,2,4-triazole 11.

As shown in Scheme 3, compound 14 can be obtained by the alkylation of intermediate 12 (e.g. compounds 5 and 10) with 2-(triphenylmethyl)-5-[4'-(bromomethyl)biphenyl-2-yl]tetrazole 13 under basic condition. Compound 13 can be prepared in accordance with e.g. J. Org. Chem., 1991, 56, 2395–2400 or J. Med. Chem. 1991, 34, 2919–2922. Then, 1,2,4-triazin-5-one biphenyl compounds of formula (I) can be obtained by removing the triphenylmethyl protecting group of compound 14 under acidic condition. As shown in Scheme 4, alkyl amidine hydrochloride 15 can be condensed with dimethyl 2-(2'-phenylethyl)malonate 16 under basic condition to 2-alkyl-5-(2'-phenylethyl)-6-hydroxy-4(3H)-pyrimidinone 17. Compound 18 can then be obtained by heating compound 17 with a compound of formula $POR_3$ wherein $R_3$ is halogen or phosphorylation with phosphonyl chloride and partially hydrolyzing the resultant intermediate in dioxane and basic solution. The compound of formula (I) wherein A represents C—$R_3$ can then be obtained by alkylating compound 18 and 2-(triphenylmethyl)-5-[4'-(bromomethyl)biphenyl-2-yl-tetrazole 13 under basic condition and deprotecting triphenylmethyl protecting group in acidic solution.

If desired, the compounds of formula (I) can be converted into the pharmaceutically salts thereof by conventional methods.

In accordance with the administration routes, the compounds of formula (I) and the pharmaceutically acceptable salts thereof can be admixed with pharmaceutically acceptable carriers, excipients and diluents to form various pharmaceutical preparations, such as tablets, capsules, powders, solutions, suspensions, syrups or emulsions for oral administration; and injections for parenteral administrations, e.g. subcutaneous, intramuscular, intravenous or intraperitoneal injections.

Typically, the solid formulations for oral administration may comprise carriers or diluents such as lactose, starch, cellulose derivatives, magnesium stearate, stearic acid and the like. Both tablets and capsules can be formulated to be in slow-released forms to continuously release the active ingredient in a set period. In addition, tablets may be coated with sugar or film coating to mask undesirable order, or prevent oxidation, or with enteric coating to selectively disintergrate in gastrointestine.

To increase the compliance of patients, oral solutions may comprise coloring agents and flavoring agents.

Carriers suitable for use in parenteral solutions include water, oil, saline, dextrose and relevant sugar solutions, and diols, such as ethylene or propylene alcohol. Preferably, parenteral solutions comprise the water soluble salts of active compounds, and stabilizing agents. If necessary, a buffering agent may be used. Suitable stabilizing agents include sodium hydrogen sulfite, sodium sulfite or antioxidants such as vitamin C. Citric acid and the salts thereof and EDTA may also be used. In addition, the solutions may also contain preservatives, such as methyl or propyl para-hydroxy benzoate and chloro butanol chloride.

The pharmaceutical composition of the compounds of formula (I) and their pharmaceutically acceptable salts may also contain other compatible active ingredients known to be useful in treating cardiovascular diseases, such as diuretics and the like.

The dosage of the compounds of formula (I) and their pharmaceutically acceptable salts varies in accordance with the age and weights of patients, the specific diseases to be treated, the progresses and complications, the frequency of administrations and the expected effects. Typically, the compounds of formula (I) and the pharmaceutically acceptable salts thereof are administered at a daily dosage of 30 to 100 mg/kg of body weight.

PREPARATIVE EXAMPLES

Example 1

Preparation of benzimidate hydrochloride

A solution of benzonitrile (20 g, 0.194 mol) in methanol (8 ml) was bubbled with gaseous HCl to saturation. The solution was allowed to stand overnight, and then a pale yellow solid was found. The solid was triturated with ether, filtered, washed with ether, and dried to yield beige solid product (32 g, 96%).

Example 2

Preparation of benzhydrazidine

Benzimidate hydrochloride (10 g, 58.3 mmol) was treated with 100 ml of sodium hydroxide (5%), and extracted with 100 ml of ether. After dried, filtered and concentrated, the pale yellow liquid benzimidate free base (8.56 g, 63.4 mmol) was obtained. Treated with hydrazine anhydried, the mixture was stirred at a temperature of 0° C. for 2 days. After concentration of the solution, a white solid product (4.23 g, 49%) was obtained by re-crystallization from ethanol/isopropyl ether.

Example 3
Preparation of 6-methyl-3-phenyl-1,2,4-triazine-5-one

Benzhydrazidine (0.6 g, 4.4 mmol) in 20 ml of isopropanol was slowly added to methyl pyruvate (0.45 ml, 4.9 mmol) in 5 ml of isopropanol. The resulting solution was continuously stirred at room temperatures for 6 hours, and heated to a reflux temperature overnight. After concentration of the solution, a white solid product (34.7 mg) was obtained by recrystallization from ethanol/isopropyl ether. Another drop of white solid (305.7 mg) was obtained from mother liquid by column chromatography. Two parts were collected (340.4 mg, 41%), and uncyclized by-product was also obtained (542.1 mg, 56%). The desired products: $^1$H NMR (CDCl$_3$ & DMSO-d$_6$, δ) 8.15–8.10 (m, 2H), 7.60–7.48 (m, 3H), 2.36 (s, 3H).

Example 4
Preparation of 3,6-diphenyl-1,2,4-triazin-5-one
Method 1

Using the procedure similar to Example 3, methylbenzoyl formate (0.95 ml, 6.5 mmol) in 5 ml of isopropanol was slowly added to benzhydrazidine (0.8 g, 5.9 mmol) in 10 ml of isopropanol. The resulting solution was continuously stirred at room temperatures for 6 hours, and heated to a reflux temperature overnight. After concentration of the solution, a white solid product (0.95 g, 64.5%) was obtained by recrystallization from ethyl acetate/ethanol.
Method 2

Benzhydrazidine (0.8 g, 5.9 mmol) and benzoyl formic acid (1.0 g, 6.5 mmol) were dissolved in 10 ml of DMF. After stirring for 12 hours at room temperatures, the solution was heated to reflux temperature overnight. After concentration of the solution, a white solid product (0.79 g, 54%) was obtained by recrystallization from ethyl acetate/ethanol. $^1$H NMR (CDCl$_3$ & DMSO-d$_6$, δ) 8.26–8.13 (m, 4H), 7.67–7.60 (m, 3H), 7.59–7.48 (m, 3H).

Example 5
Preparation of 3-phenyl-6-(2'-phenylethyl)-1,2,4-triazin-5-one

Benzhydrazidine (0.6 g, 4.4 mmol) in 10 ml of isopropanol was slowly added dropwise to ethyl-2-oxo-4-phenyl butanoate (1.0 g, 4.9 mmol) in 30 ml of isopropanol. The resulting mixture was heated to 60° C. After completely dissolved, the mixture was again heated to reflux temperature overnight. The solution was concentrated, and the desired white product (0.18 g, 15%) was purified by column chromatography and the other acyclic yellow by-product (1.21 g, 85%) was also obtained. The desired products: $^1$H NMR (CDCl$_3$ & DMSO-d$_6$, δ) 8.15–8.10 (m, 2H), 7.57–7.45 (m, 3H), 7.27–7.15 (m, 5H), 3.06 (s, 4H).

Example 6
Preparation of valeroylimidate hydrochloride

Gaseous HCl was introduced into valeronitrile (25 ml, 241 mmol) in methanol (10.7 ml, 265 mmol) at 0° C. under nitrogen. A white jelly material was formed on standing. Subsequently, 140 ml of ether were added and a white crystalline (20 g) was obtained. Another crop of product (3.5 g) was obtained from mother liquid. The combined yield was 23.5 g (64%).

Example 7
Preparation of valeroyl N-formyl hydrazidine

Ethyl formate (8.0 ml, 0.1 mol) in 5 ml of ethanol was slowly added dropwise to anhydrous hydrazine (3.2 ml, 0.1 mol) in 12 ml of ethanol at 0° C., then the solution was stirred for 5 hours. A white solid was formed on standing, then filtered, and the formyl hydrazidine (6.05 g, 100%) was obtained.

Valeroylimidate hydrochloride (5 g, 33 mmol) was treated with 50 ml of sodium hydroxide (5%) and extracted with 75 ml of ether. The solution was dried, filtered, and concentrated, and a clear liquid of valeroylimidate free base (3.48 g, 92%) was obtained. Valeroylimidate free base (1.15 g, 0.01 mol) was dissolved in 10 ml ethanol, added to formyl hydrazide (0.6 g, 0.01 mol) at 0° C., then stirring 3 hrs, and a white solid was formed. After filtered, recrystallized, a white product (1.27 g, 88%) was obtained.

Example 8
Preparation of 3-butyl-6-methyl-1,2,4-triazin-5-one

Methyl pyruvate (0.4 ml, 4.35 mmol) in 10 ml of isopropanol was added dropwise to valeroyl N-formyl hydrazidine (500 mg, 3.5 mmol) in 20 ml of isopropanol. The resulting mixture was stirred for 4 hours and then heated to reflux temperature overnight. The solution was concentrated, and a yellow solid product (75.4 mg, 13%) was purified by column chromatography. $^1$H NMR (CDCl$_3$, δ) 2.74 (t, 2H, J=7.6 Hz), 2.34 (s, 3H), 1.84–1.69 (m, 2H), 1.48–1.25 (m, 2H), 0.91 (t, 3H, J=7.2 Hz).

Example 9
Preparation of 3-butyl-6-phenyl-1,2,4-triazin-5-one

Valeroyl N-formyl hydrazidine (500 mg, 3.5 mmole) was mixed with p-toluenesulphonic acid (865 mg, 4.55 mmole) then dissolved in 4 ml DMF, and the mixture was stirred at room temperature for 1 hour. The benzoylformic acid (0.59 g, 3.85 mmole) dissolved in DMF (3 ml) was slowly added. The mixture was stirred for 4 hours, and heated to reflux temperature overnight. The solution was concentrated, and the product was obtained as white powder (0.50 g, 63%) after purified by column chromatography. $^1$H NMR (DMSO-d$_6$, δ) 8.08–8.02 (m, 2H), 7.40–7.31 (m, 3H), 2.59 (t, 2H, J=7.6 Hz), 1.79–1.68 (m, 2H), 1.43–1.25 (m, 2H), 0.87 (t, 3H, J=7.2 Hz).

Example 10
Preparation of 3-butyl-6-benzyl-1,2,4-triazin-5-one

To a reaction flask, valeroyl N-formyl hydrazidine (2.0 g, 14 mmole), p-toluenesulphonic acid (6.12 g, 32.2 mmole), phenyl pyruvic acid (3.67 g, 22.4 mmole) and DMF (18 ml) were added. The mixture was stirred at room temperature for 4 hours, and then heated to reflux temperature overnight. The solution was evaporated, the residue was purified successively by column chromatography and washed with ethyl acetate/n-hexane (1:2), to give the final product as a white powder (388 mg, 12%). $^1$H NMR (CDCl$_3$, δ) 7.35–7.20 (m, 5H), 4.02 (s, 2H), 2.64 (t, 2H, J=7.6 Hz), 1.76–1.61 (m, 2H), 1.37–1.26 (mn, 2H), 0.86 (t, 3H, J=7.2 Hz).

Example 11
Preparation of 3-butyl-6-(2'-phenylethyl)-1,2,4-triazin-5-one

To a reaction flask, valeroyl N-formyl hydrazidine (1.0 g, 7 mmole), p-toluenesulphonic acid (1.33 g, 7 mmole), and DMF (5 ml) were added. 2-Oxo-4-phenyl butyric acid (1.37 g, 7.7 mmole) in DMF (5 ml) was added to the mixture. The mixture was stirred at room temperature for 2 hours, and then heated to reflux temperature overnight. A yellow solid was obtained after concentrated the solution and purified by column chromatography. The solid was washed with ethyl acetate/n-hexane (1:1) and the final product was obtained as white powder (808 mg, 45%). $^1$H NMR (CDCl$_3$, δ) 7.36–7.04 (m, 5H), 3.03 (s, 4), 2.71 (t, 2H, J=7.5 Hz), 1.80–1.74 (m, 2H), 1.41–1.36 (m, 2H), 0.71 (t, 3H, J=7.2 Hz).

Example 12

Preparation of 2-butyl-5-(2'-phenylethyl)-6-hydroxy-4(3H)-pyrimidinone

To a mixture of n-valeroylamidine hydrochloride (15.5 g, 0.114 mmole) and dimethyl 2-(2'-phenylethyl)malonate (26.8 g, 0.114 mole) was added the solution of sodium ethoxide obtained by adding sodium (7.84 g, 0.34 mole) to ethanol (320 mol). The mixture was refluxed for 4 hours, then concentrated, filtered and acidified with 10% hydrochloride. After filtration, the product as white powder was obtained (29 g, 94%). M.P.: 230° C. (dec.).

Example 13

Preparation of 6-chloro-2-butyl-5-(2'-phenylethyl)-pyrimidinone

The product of Example 12 (4.3 g, 15.8 mmole) was mixed with phosphoryl chloride (10 ml, 0.107 mmole), and heated to reflux temperature for 50 min. Ice water (50 g) was poured into the mixture, and a product was obtained as white powder, which was filtered and washed with n-hexane, there was obtained 4,6-dichloro-2-butyl-5-(2'-phenylethyl)-pyrimidine (4.7 g, 96%).

The above product (5.97 g, 19.2 mmole) was added to dioxane (30 ml) and a sodium hydroxide solution (prepared from 1.92 g sodium hydroxide and 10 ml water), and heated to refluxed for 4 hours. The solution was concentrated and extracted with ether. The aqueous phase was acidified with 10% hydrochloride and the desired pyrimidinone was obtained (2.8 g, 50%). $^1$H NMR (CDCl$_3$, δ) 7.30–7.20 (m, 5H), 2.86 (m, 4H), 2.69 (t, 2H, J=8.0 Hz), 1.76 (m, 2H), 1.46 (m, 2H), 0.97 (t, 3H, J=8.0 Hz); MS (EI) m/e: 291 (M$^+$, 38).

The following examples are provided to further illustrate the synthesis of the compounds of the invention.

Example I 6-methyl-3-phenyl-5-oxo-2-[[2'-(triphenylmethyltetrazol-5-yl)biphenyl-4-yl]methyl]-1,2,4-triazine—(A)
6-methyl-3-phenyl-5-oxo-4-[[2'-(triphenylmethyltetrazol-5-yl)biphenyl-4-yl]methyl]-1,2,4-triazine—(B)
6-methyl-3-phenyl-5-[[2'-(triphenylmethyltetrazol-5-yl)biphenyl-4-yl]methoxy]-1,2,4-triazine—(C)

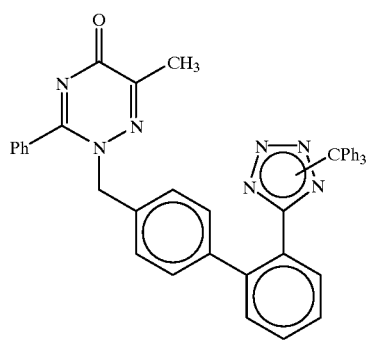

(A)

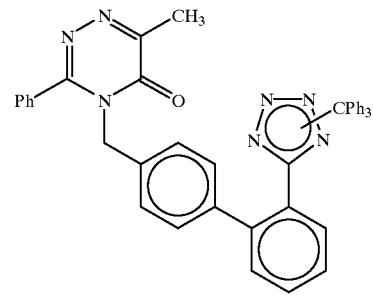

(B)

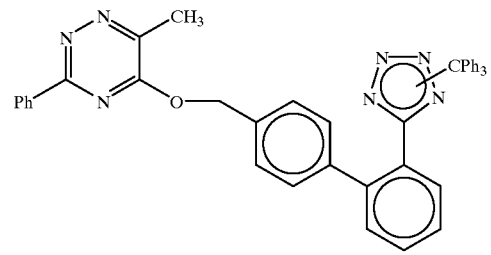

(C)

To a flask was added 2-(triphenylmethyl)-5-[4'-(bromomethyl)-biphenyl-2-yl]tetrazole (571 mg, 1.03 mmol) and cesium carbonate (668 mg, 2.05 mmol). Then, the compound of example 3 (128 mg, 0.68 mmol) in DMF (3 ml) was injected into the flask, and stirred overnight at room temperature. A large quantity of ethyl acetate was added, filtered and then the filtrate was washed with saturated brine. After dried, filtered and concentrated, product A (31 mg, 7%), product B (38 mg, 8%) and product C (164 mg, 38%) were obtained.

Product A: $^1$H NMR (CDCl$_3$, δ) 7.89–7.84 (m, 1H), 7.45–7.16 (m, 20H), 7.00–6.87 (m, 8H), 5.01 (s, 2H), 2.56 (s, 3H).

Product B: $^1$H NMR (CDCl$_3$, δ) 7.96–7.91 (m, 1H), 7.50–7.41 (m, 8H), 7.31–7.18 (m, 10H), 7.12–7.08 (m, 2H), 6.94–6.80 (m, 8H), 5.08 (s, 2H), 2.37 (s, 3H).

Product C: $^1$H NMR (CDCl$_3$, δ) 8.53–8.49 (m, 2H), 8.00–7.95 (m, 1H), 7.56–7.42 (m, 5H), 7.32–7.17 (m, 14H), 6.94–6.80 (m, 8H), 5.25 (s, 2H), 2.56 (s, 3H).

Example II 6-methyl-3-phenyl-5-oxo-2-[[2'-(1H-tetrazol-5-yl)biphenyl-4-yl]methyl]-1,2,4-triazine—(D)
6-methyl-3-phenyl-5-oxo-4-[[2'-(1H-tetrazol-5-yl)biphenyl-4-yl]methyl]-1,2,4-triazine—(E)

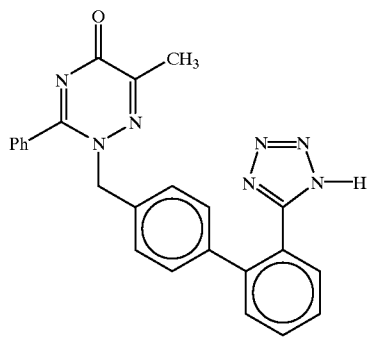 (D)

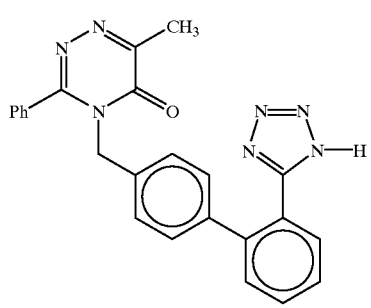 (E)

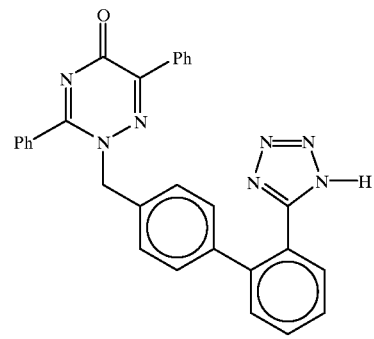 (F)

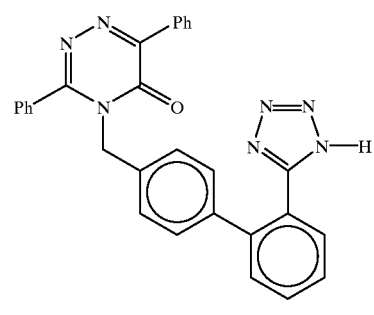 (G)

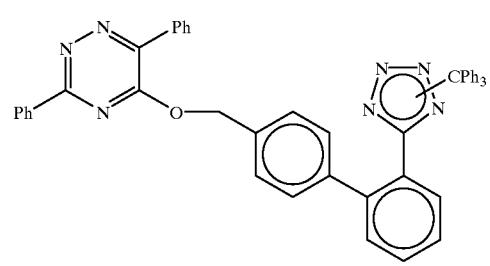 (H)

Compound (A) of Example I (20 mg, 0.03 mmol) was dissolved in tetrahydrofuran (2 ml), then hydrochloric acid (10%) was added dropwise and stirring for overnight. After concentration, distilled water (2 ml) was added and the pH was adjusted to 6–7 with saturated sodium bicarbonate solution. The solution was extracted with ethyl acetate, dried, filtered and concentrated to give a yellow solid, and then purified by column chromatography, yielding product (D) (5.6 mg 44%).

Following the similar method, Compound (E) (5.3 mg, 28%) can be obtained from Compound (B) (30 mg, 0.045 mmol) prepared in Example I (30 mg, 0.045 mmol).

Product D: $^1$H NMR (CDCl$_3$, δ) 7.87–7.84 (m, 1H), 7.59–7.26 (m, 9H), 6.99–6.95 (m, 2H), 6.80–6.76 (m, 2H), 5.01 (s, 2H), 2.49 (s, 3H); MS (FAB): m/e 422 (M+1, 100).

Product E: $^1$H NMR (CDCl$_3$, δ) 7.74–7.70 (m, 1H), 7.54–7.26 (m, 9H), 6.94–6.90 (m, 2H), 6.80–6.76 (m, 2H), 5.07 (s, 2H), 2.31 (s, 3H); MS (FAB): m/e 422 (M+1, 100).

Example III 3,6-diphenyl-5-oxo-2-[[2'-(1H-tetrazol-5-yl)biphenyl-4-yl]methyl]-1,2,4-triazine—(F)
3,6-diphenyl-5-oxo-4-[[2'-(1H-tetrazol-5-yl)biphenyl-4-yl]methyl]-1,2,4-triazine—(G)
3,6-diphenyl-5-[[2'-(triphenylmethyltetrazol-5-yl)biphenyl-4-yl]methoxy]-1,2,4-triazine—(H)

Using the method similar to Examples I and II, the compound of example 4 (3.78 mmol) and 2-(triphenylmethyl)-5-[4'-(bromomethyl)biphenyl-2-yl]tetrazole (4.53 mmol) were subjected to N-alkylation under basic conditions (7.55 mmol of cesium carbonate in DMF). Then, the triphenylmethyl protecting group was removed by acidic aqueous solution (10% hydrochloric acid and THF), yielding product F (13%), product G (17%), and product H (13%).

Product F: $^1$H NMR (d$_4$-MeOH, δ) 8.15–8.10 (m, 2H), 7.58–7.25 (m, 13H), 6.92–6.88 (m, 2H), 6.78–6.74 (m, 2H), 5.08 (s, 2H); MS (FAB): m/e 483 (M+1, 79).

Product G: $^1$H NMR (d$_4$-MeOH, δ) 8.23–8.17 (m, 2H), 7.68–7.47 (m, 13H), 7.11–6.99 (m, 4H), 5.31 (s, 2H).

Product H: $^1$H NMR (CDCl$_3$, δ) 8.63–8.58 (m, 2H), 8.22–8.17 (m, 2H), 8.00–7.95 (m, 1H), 7.60–7.39 (m, 9H), 7.32–7.18 (m, 13H), 6.94–6.90 (m, 6H), 5.65 (s, 2H).

Example IV 6-(2'-phenylethyl)-3-phenyl-5-oxo-2-[[2'-(1H-tetrazol-5-yl)biphenyl-4-yl]methyl]-1,2,4-triazine—(I)
6-(2'-phenylethyl)-3-phenyl-5-[[2'-(triphenylmethyltetrazol-5-yl)biphenyl-4-yl]methoxy]-1,2,4-triazine—(J)

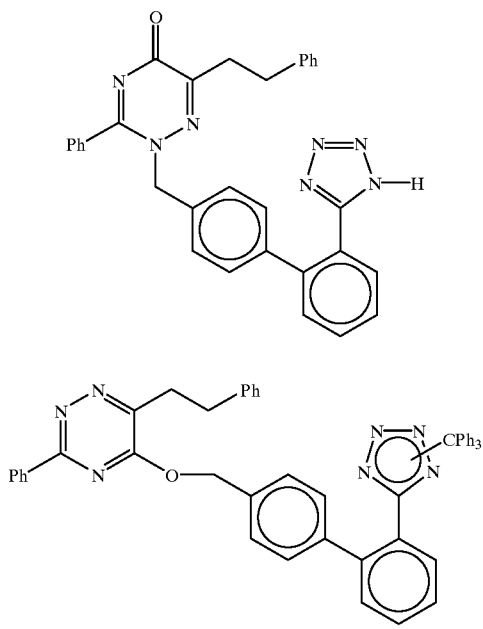
(I)

(J)

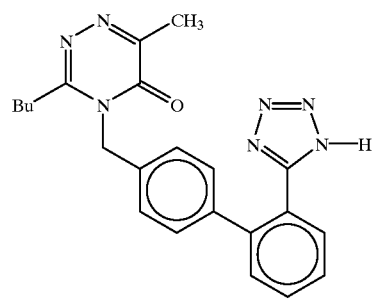
(L)

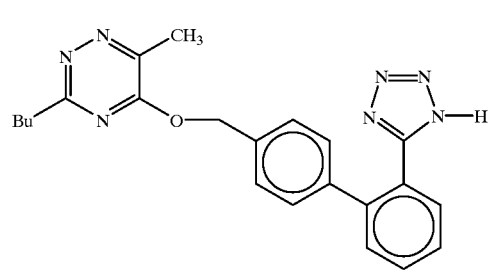
(M)

Using the method similar to Examples I and II, the compound of example 5 (0.62 mmol) and 2-(triphenylmethyl)-5-[4'-(bromomethyl)biphenyl-2-yl] tetrazole (0.74 mmol) were subjected to N-alkylation under basic conditions (1.23 mmol of cesium carbonate in DMF). Then, the triphenylmethyl protecting group was removed by acidic aqueous solution (10% hydrochloric acid and THF), yielding product I (16%) and product J (44%).

Product I: $^1$H NMR (CDCl$_3$, δ) 7.78–7.74 (m, 1H), 7.51–7.19 (m, 4H), 6.90–6.86 (m, 2H), 6.63–6.59 (m, 2H), 5.02 (s, 2H), 3.03(s, 4H); MS (FAB): m/e 512 (M+1, 52).

Product J: $^1$H NMR (CDCl$_3$, δ) 7.98–7.95 (m, 1H), 7.54–7.47 (m, 8H), 7.25–7.19 (m, 22H), 6.91–6.87 (m, 7H), 5.48 (s, 2H), 3.27–3.19 (br. s, 4H).

Example V 6-methyl-3-butyl-5-oxo-2-[[2'-(1H-tetrazol-5-yl)biphenyl-4-yl]methyl]-1,2,4-triazine—(K)
6-methyl-3-butyl-5-oxo-4-[[2'-(1H-tetrazol-5-yl)biphenyl-4yl]methyl]-1,2,4-triazine—(L)
6-methyl-3-butyl-5-[[2'-(1H-tetrazol-5-yl)biphenyl-4-yl]methoxy]-1,2,4-triazine—(M)

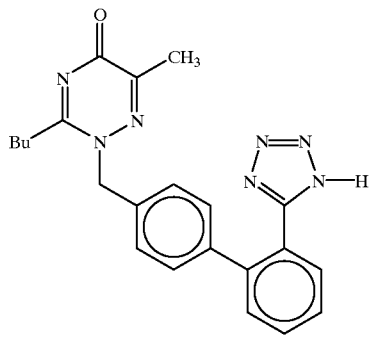
(K)

Using the method similar to Examples I and II, the compound of example 8 (2.12 mmol) and 2-(triphenylmethyl)-5-[4'-(bromomethyl)biphenyl-2-yl] tetrazole (2.55 mmol) were subjected to N-alkylation under basic conditions (3.19 mmol of cesium carbonate in DMF). Then, the triphenylmethyl protecting group was removed by acidic aqueous solution (10% hydrochloric acid and THF), yielding product K (45%), product L (17%), and product M (16%).

Product K: $^1$H NMR (CDCl$_3$, δ) 7.83 (d, 1H, J=7.2 Hz), 7.57–7.39 (m, 3H), 7.11 (q, 4H, J=17 Hz, 8.0 Hz), 5.22 (s, 2H), 2.56 (t, 2H, J=7.6 Hz), 2.23 (s, 3H), 1.60–1.57 (m, 2H), 1.35–1.25 (m, 2H), 0.83 (t, 3H, J=7.2 Hz); m.p.: 88–92° C.; MS (FAB): m/e 402 (M+1, 81).

Product L: $^1$H NMR (CDCl$_3$, δ) 7.86 (d, 1H, J=7.6 Hz), 7.60–7.39 (m, 3H), 7.08 (q, 4H, J=13 Hz, 8.4 Hz), 5.18 (s, 2H), 2.68 (t, 2H, J=7.6 Hz), 2.38 (s, 3H), 1.70–1.58 (m, 2H), 1.41–1.25 (m, 2H), 0.87 (t, 3H, J=7.2 Hz); m.p.: 120–124° C.; MS (EI): m/e 401 (M$^+$, 7.7); HRMS (C$_{22}$H$_{23}$N$_7$O) Calculated: 401.1964, Found: 401.1965.

Product M: $^1$H NMR (CDCl$_3$, δ) 7.91 (d, 1H, J=7.6 Hz), 7.62–7.41 (m, 3H), 7.24 (d, 2H, J=7.6 Hz), 7.07 (d, 2H, J=7.6 Hz), 4.64 (s, 2H), 2.65 (t, 2H, J=7.6 Hz), 2.29 (s, 3H), 1.78–1.63 (m, 2H), 1.39–1.26 (m, 2H), 0.87 (t, 3H, J=7.2 Hz); m.p.: 104–108° C.

Example VI 6-phenyl-3-butyl-5-oxo-2-[[2'-(1H-tetrazol-5-yl)biphenyl-4-yl]methyl]-1,2,4-triazine—(N)
6-phenyl-3-butyl-5-oxo-4-[[2'-(1H-tetrazol-5-yl)biphenyl-4-yl]methyl]-1,2,4-triazine—(O)
6-phenyl-3-butyl-5-[[2'-(triphenylmethyltetrazol-5-yl)biphenyl-4-yl]methoxy]-1,2,4-triazine—(P)

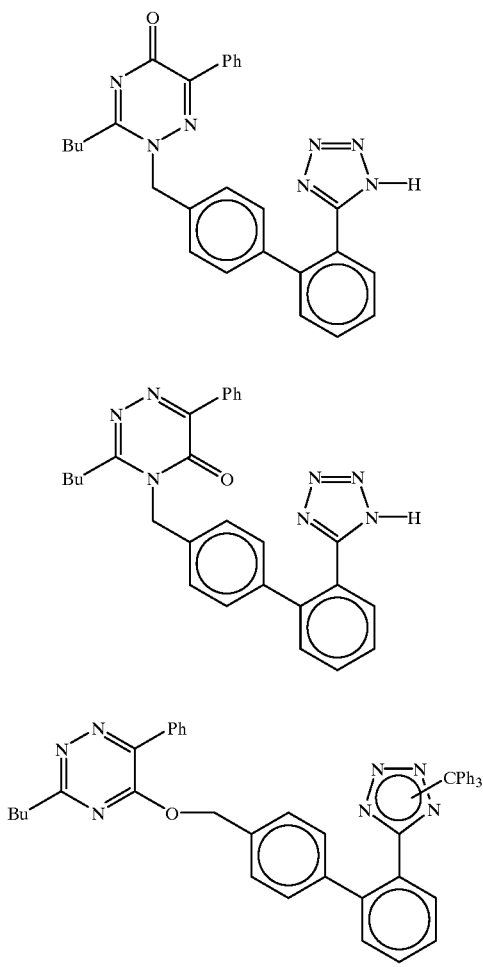

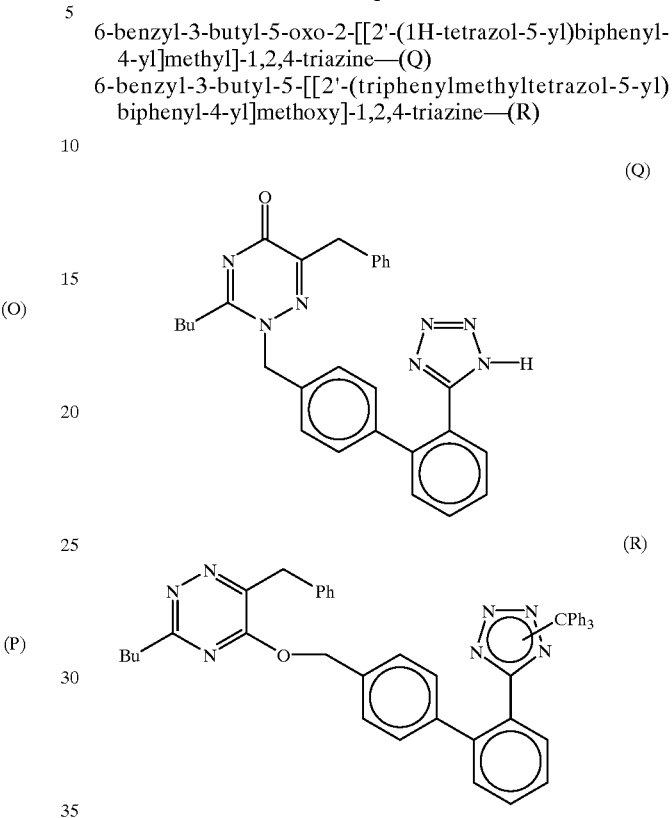

Using the method similar to Examples I and II, the compound of example 9 (4.02 mmol) and 2-(triphenylmethyl)-5-[4'-(bromomethyl)biphenyl-2-yl] tetrazole (4.18 mmol) were subjected to N-alkylation under basic conditions (8.03 mmol of cesium carbonate in DMF). Then, the triphenylmethyl protecting group was removed by acidic aqueous solution (10% hydrochloric acid and THF), yielding product N (56.6%), product O (12.8%), and product P (8.8%).

Product N: $^1$H NMR(CDCl$_3$, δ) 8.12–8.07 (m, 2H), 7.80–7.76 (m, 1H), 7.58–7.35 (m, 6H), 7.09 (s, 4H), 5.25 (s, 2H), 2.55 (t, 2H, J=7.6 Hz), 1.62–1.50 (m, 2H), 1.33–1.21 (m, 2H), 0.81 (t, 3H, J=7.2 Hz); m.p.: 117–121° C.

Product O: $^1$H NMR (CDCl$_3$, δ) 8.09–8.05 (m, 2H), 8.04–7.85 (m, 1H), 7.61–7.32 (m, 6H), 7.08 (s, 4H), 5.20 (s, 2H), 2.70 (t, 2H, J=7.6 Hz), 1.73–1.61 (m, 2H), 1.42–1.25 (m, 2H), 0.88 (t, 3H, J=7.2 Hz); m.p.: 148–151° C.; MS (EI): m/e 463 (M$^+$, 10); HRMS (C$_{27}$H$_{25}$N$_7$O) Calculated: 463.2121, Found: 463.2107.

Product P: $^1$H NMR (CDCl$_3$, δ) 8.09–8.04 (m, 2H), 7.96–7.92 (m, 1H), 7.51–7.12 (m, 19H), 6.91–6.86 (m, 6H), 5.48 (s, 2H), 3.04 (t, 2H, J=7.6 Hz), 1.92–1.85 (m, 2H), 1.52–1.41 (m, 2H), 0.99 (t, 3H, J=7.2 Hz); m.p.: 138–140° C.(dec.); MS (EI): m/e 706 (M+1, 2); HRMS (C$_{46}$H$_{39}$N$_7$O) Calculated: 705.3216, Found: 705.3259.

Example VII 6-benzyl-3-butyl-5-oxo-2-[[2'-(1H-tetrazol-5-yl)biphenyl-4-yl]methyl]-1,2,4-triazine—(Q)

6-benzyl-3-butyl-5-[[2'-(triphenylmethyltetrazol-5-yl)biphenyl-4-yl]methoxy]-1,2,4-triazine—(R)

Using the method similar to Examples I and II, the compound of example 10 (1.74 mmol) and 2-(triphenylmethyl)-5-[4'-(bromomethyl)biphenyl-2-yl] tetrazole (2.60 mmol) were subjected to N-alkylation under basic conditions (3.47 mmol of cesium carbonate in DMF). Then, the triphenylmethyl protecting group was removed by acidic aqueous solution (10% hydrochloric acid and THF), yielding product Q (21%) and product R (12%).

Product Q: $^1$H NMR (CDCl$_3$, δ) 7.85–7.83 (m, 1H), 7.52–7.37 (m, 4H), 7.25–7.13 (m, 1H), 7.10–7.05 (m, 4H), 5.15 (s, 2H), 3.95 (s, 2H), 2.52 (t, 2H, J=7.6 Hz), 1.57–1.55 (m, 2H), 1.25–1.23 (m, 2H), 0.81 (t, 3H, J=7.2 Hz); m.p.: 110–114° C.

Product R: $^1$H NMR (CDCl$_3$, δ) 7.97–7.92 (m, 1H), 7.50–7.31 (m, 3H), 7.28–7.00 (m, 18H), 6.92–6.87 (m, 6H), 5.30 (s, 2H), 4.20 (s, 2H), 2.93 (t, 2H, J=7.6 Hz), 1.84–1.73 (m, 2H), 1.47–1.36 (m, 2H), 0.95 (t, 3H, J=7.2 Hz); m.p.: 101–105° C.

Example VIII 6-(2'-phenylethyl)-3-butyl-5-oxo-2-[[2'-(1H-tetrazol-5-yl)biphenyl-4-yl]methyl]-1,2,4-triazine—(S)

6-(2'-phenylethyl)-3-butyl-5-oxo-4-[[2'-(1H-tetrazol-5-yl)biphenyl-4-yl]methyl]-1,2,4-triazine—(T)

6-(2'-phenylethyl)-3-butyl-5-[[2'-(triphenylmethyltetrazol-5-yl)biphenyl-4-yl]methoxy]-1,2,4-triazine—(U)

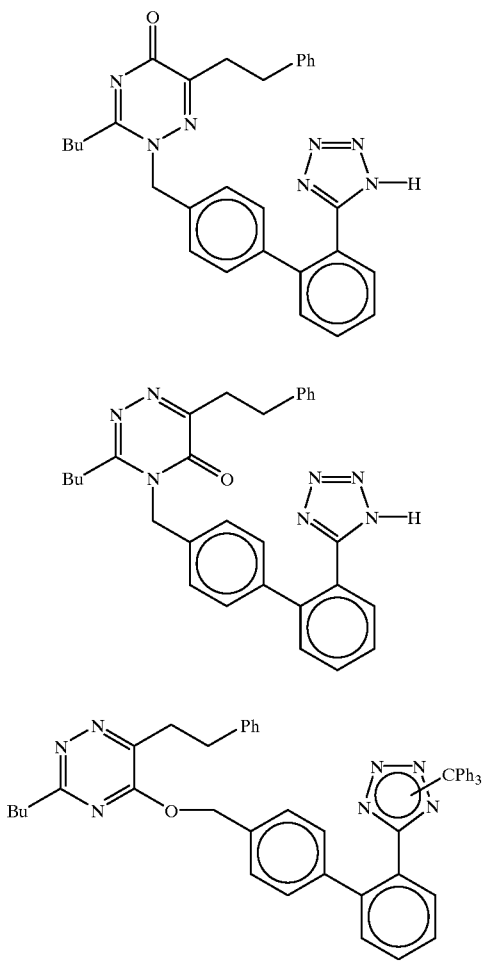

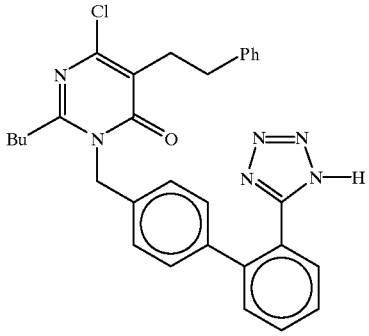

Using the method similar to Examples I and II, the compound of example 11 (3.71 mmol) and 2-(triphenylmethyl)-5-[4'-(bromomethyl)biphenyl-2-yl]tetrazole (4.45 mmol) were subjected to N-alkylation under basic conditions (7.42 mmol of cesium carbonate in DMF). Then, the triphenylmethyl protecting group was removed by acidic aqueous solution (10% hydrochloric acid and THF), yielding product S (47%), product T (20%), and product U (11%).

Product S: $^1$H NMR (CDCl$_3$, δ) 7.88–7.87 (m, 1H), 7.57–7.55 (m, 1H), 7.50–7.48 (m, 1H), 7.47–7.40 (m, 1H), 7.22–7.11 (m, 7H), 6.93–6.92 (m, 2H), 5.14 (s, 2H), 3.00 (s, 4H), 2.49 (t, 2H, J=7.5 Hz), 1.60–1.54 (m, 2H), 1.31–1.25 (m, 2H), 0.82 (t, 3H, J=7.5 Hz); m.p.: 76–78° C.; MS (FAB): m/e 492 (M+1, 57); HRMS (C$_{29}$H$_{30}$N$_7$O) Calculated: 492.2512, Found: 492.2494.

Product T: $^1$H NMR (CDCl$_3$, δ) 7.91–7.90 (m, 1H), 7.60–7.59 (m, 1H), 7.52–7.51 (m, 1H), 7.43–7.41 (m, 1H), 7.28–7.26 (m, 2H), 7.22–7.19 (m, 3H), 7.14–7.12 (m, 2H), 7.05–7.04 (m, 2H), 5.18 (s, 2H), 3.10–3.09 (m, 2H), 3.04–3.02 (m, 2H), 2.68 (t, 2H, J=7.5 Hz), 1.71–1.68 (m, 2H), 1.44–1.36 (m, 2H), 0.90 (t, 3H, J=7.5 Hz); m.p.: 80–82° C.; MS (FAB): m/e 492 (M+1, 43); HRMS (C$_{29}$H$_{30}$N$_7$O) Calculated: 492.2512, Found: 492.2522.

Product U: $^1$H NMR (CDCl$_3$, δ) 8.04–7.95 (m, 1H), 7.46–7.40 (m, 2H), 7.39–7.30 (m, 1H), 7.29–7.16 (m, 18H), 6.90–6.88 (m, 6H), 5.34 (s, 2H), 3.17–3.14 (m, 2H), 2.95 (t, 2H, J=7.5 Hz), 1.84–1.81 (m, 2H), 1.45–1.26 (m, 2H), 0.96 (t, 3H, J=7.2 Hz); m.p.: 148–150° C.(dec.).

Example IX 2-butyl-5-(2'-phenylethyl)-6-chloro-3-[[2'-(1H-tetrazol-5-yl)biphenyl-4-yl]methyl]-4(3H)-pyrimidinone—(V)

The compound of example 13 (1.7 mmol) and 2-(triphenylmethyl)-5-[4'-(bromomethyl)biphenyl-2-yl]tetrazole (2 mmol) were mixed under basic conditions (4 mmol of cesium carbonate in DMF), and then the mixture was subjected to N-alkylation. Next, the triphenylmethyl protecting group was removed by acidic aqueous solution (10% hydrochloric acid and THF), yielding the desired product V (42%).

Product V: $^1$H NMR (CDCl$_3$, δ) 8.00 (d, 1H, J=8.0 Hz), 7.60–7.00 (m, 12H), 5.26 (s, 2H), 2.88 (m, 4H), 2.66 (t, 2H, J=7.2 Hz), 1.72 (m, 2H), 1.26 (m, 2H), 0.96 (t, 3H, J=7.2 Hz); MS (EI): m/e 524.4 (M$^+$, 20).

The binding affinity of the compounds of the above Examples I to IX to angiotensin II receptor was tested. The procedures and results are as follows:

Assay for the Binding Affinity to Angiotensin II Receptor (1) Reagents

The antagonistic activity of angiotensin II receptor was assayed by Angiotensin II Type I Receptor Kit (NED-014 NENQUEST Drug Discovery System, NEN Research Products, Massachusettes, USA). The kit comprises Angiotensin II Type I Receptor Concentrate, radioligand [$^{125}$I]-Sar$^1$,Ile$^8$-Angiotensin II Concentrate (5 Ci), Standard Concentrate (DuP 753, 10 M), Diluent Concentrate, and Filter-Soak Concentrate. In accordance with the manual of NED-014 kit, the Radioligand Concentrate, Receptor Concentrate and Filter-Soak Concentrate were diluted with deionized water, and stored under suitable temperatures (-70° C. or ambient temperature).

(2) Equipment

1. Filter Device: Hoefer FH 224 V, Hoefer Scientific Instruments Inc., California, USA; Vacuum pressure=15 in. Hg.

2. γ-Counter: Beckman 5500, Beckman Instruments Inc., Montana., USA.

(3) Procedures

The reagents were thawed on ice on the day of assays. Two sets of tubes, each with two tubes, were used, one for non-specific binding (NSB) and the other for total binding (TB). A series of standard solutions (with the final concentrations of 0.5, 1, 2, 5, 10, 20, 50 and 100 nM) were prepared. The tested compounds were dissolved and diluted to 500 nM for preliminary screening. The compounds which were found to be effective in the preliminary screening were used to prepare a series of various concentrations in accordance with the screening results. To the NSB tubes were added 25 μL Standard Concentrate solutions, to the TB tubes were added 25 μL Diluent Concentration, and to other tubes were added 25 μL the solutions of tested compounds. Then, 25 μL radioligand were added to each tube (including the two tubes for total counts, TC). The two TC tubes were used later for the determination of the dosage of radioligand added to each tube. To the rest tubes, 200 μL Receptor Concentration solutions were added. The tubes were allowed to stand for 3 hours to reach equibilium completely. Filter papers (Sigma Catalog No. 1822024) were soaked in the Filter-Soak solution, and placed in the filter device. The contents in the tubes were poured onto the filter papers, and washed with saline twice. The slightly dry filter papers were placed into the γ-counter and counted with two minutes counter.

(4) Calculation

The data are expressed as counts per minute (CPM). Net CPM for Specific Binding of standards or tested compounds is defined as the CPM thereof minus that of NSP and calculated by equation 1:

$$CPM_{net} = CPM_{tested\ compounds\ or\ standard} - CPM_{non-specific\ binding} \quad \text{equation 1}$$

With the above equation, the Net CPM for Specific Binding of tested compounds and standards can be obtained.

Inhibition (% $B/B_0$) is defined as the net CPM for Specific Binding over that of standard at 0 concentration and calculated by equation 2:

$$\text{Inhibition (\% } B/B_0\text{) of tested compound} = CPM_{net} \text{ of standard at 0 concentration} \quad \text{equation 2}$$

$IC_{50}$ is defined as the concentration of compound corresponding 50% inhibition. $IC_{50}$ of tested compounds can be obtained with EBDA software by calculating the inhibition (% $B/B_0$) of the tested compounds at 7 different concentrations. In addition, as the binding activity of a series of compounds is correlated with receptors, $IC_{50}$ of the tested compounds can also be obtained by equation 3 established from known $IC_{50}$ and inhibition (% $B/B_0$) of the series compounds:

$$\% B/B_0 = -63.618 + 41.654 \times \log (IC_{50})$$

$$R^2 = 0.882 \quad \text{equation 3}$$

(5) Results

| Example No. | Compound | $IC_{50}$ (nM) |
|---|---|---|
| V | L | 309.5* |
| VI | N | 336.3 |
|  | O | 62.6* |
| VIII | S | 67.5 |
|  | T | 55.1 |
| IX | V | 72* |

*Calculated

What we claim are:

1. Compounds of formula (I):

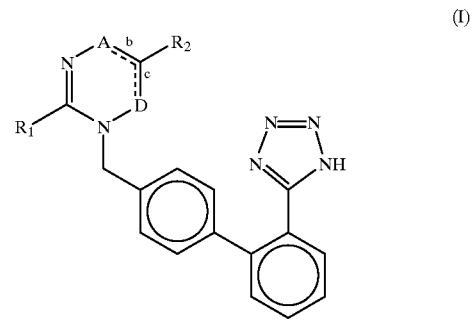

where
R₁ represents alkyl, cycloalkyl, or aryl;
R₂ represents alkyl, aryl; or arylalkyl;
one of A and D represents N, and the other represents C=O; and
one of b and c represents an optional bond; or the pharmaceutically acceptable salts thereof.

2. The compounds of claim 1 selected from the group consisting of:
6-methyl-3-phenyl-5-oxo-2-[[2'-(1H-tetrazol-5-yl)biphenyl-4-yl]methyl]-1,2,4-triazine;
6-methyl-3-phenyl-5-oxo-4-[[2'-(1H-tetrazol-5-yl)biphenyl-4-yl]methyl]-1,2,4-triazine;
3,6-diphenyl-5-oxo-2-[[2'-(1H-tetrazol-5-yl)biphenyl-4-yl]methyl]-1,2,4-triazine;
3,6-diphenyl-5-oxo-4-[[2'-(1H-tetrazol-5-yl)biphenyl-4-yl]methyl]-1,2,4-triazine;
6-(2'-phenylethyl)-3-phenyl-5-oxo-2-[[2'-(1H-tetrazol-5-yl)biphenyl-4-yl]methyl]-1,2,4-triazine;
6-methyl-3-butyl-5-oxo-2-[[2'-(1H-tetrazol-5-yl)biphenyl-4-yl]methyl]-1,2,4-triazine;
6-methyl-3-butyl-5-oxo-4-[[2'-(1H-tetrazol-5-yl)biphenyl-4-yl]methyl]-1,2,4-triazine;
6-phenyl-3-butyl-5-oxo-2-[[2'-(1H-tetrazol-5-yl)biphenyl-4-yl]methyl]-1,2,4-triazine;
6-phenyl-3-butyl-5-oxo-4-[[2'-(1H-tetrazol-5-yl)biphenyl-4-yl]methyl]-1,2,4-triazine;
6-benzyl-3-butyl-5-oxo-2-[[2'-(1H-tetrazol-5-yl)biphenyl-4-yl]methyl]-1,2,4-triazine;
6-(2'-phenylethyl)-3-butyl-5-oxo-2-[[2'-(1H-tetrazol-5-yl)biphenyl-4-yl]methyl]-1,2,4-triazine; and
6-(2'-phenylethyl)-3-butyl-5-oxo-4-[[2'-(1H-tetrazol-5-yl)biphenyl-4-yl]methyl]-1,2,4-triazine.

3. A method for treating cardiovascular diseases which comprises administering an effective amount of a compound of claim 1 to a subject in need of such treatment.

4. The method of claim 3 wherein the cardiovascular disease is hypertension or congestive heart failure.

5. A pharmaceutical composition comprising an effective amount of a compound of claim 1 or the pharmaceutically acceptable salts thereof as the active ingredient, together with a pharmaceutically acceptable carrier, excipient or diluent.

* * * * *